United States Patent [19]

Walmet

[11] Patent Number: 4,510,920

[45] Date of Patent: Apr. 16, 1985

[54] HEAT EXCHANGER MAT

[75] Inventor: Gunnar E. Walmet, Rexford, N.Y.

[73] Assignee: New York State Energy Research and Development Authority, N.Y.

[21] Appl. No.: 562,982

[22] Filed: Dec. 19, 1983

[51] Int. Cl.³ .............................................. F24J 3/02
[52] U.S. Cl. .................................. 126/415; 126/435; 126/437; 126/452; 165/1; 165/45
[58] Field of Search ........ 126/415, 416, 417, 444–446, 126/448, 435, 437, 452; 4/495, 501, 503, 543, 545, 580, 581; 165/1, 2, 45, 53

[56] References Cited

U.S. PATENT DOCUMENTS

| | | | |
|---|---|---|---|
| 3,242,503 | 3/1966 | Russo | 4/495 |
| 3,423,768 | 1/1969 | Glenn | 4/501 |
| 3,780,385 | 12/1973 | Dunn | 4/501 |
| 4,036,207 | 7/1977 | Bouse | 126/446 X |
| 4,090,496 | 5/1978 | Mallet | 126/271 |
| 4,122,846 | 10/1978 | Baumann | 4/581 X |
| 4,241,724 | 12/1980 | Hull | 126/415 |
| 4,244,351 | 1/1981 | Loeb et al. | 126/415 |
| 4,284,059 | 8/1981 | Thomason | 126/415 |

Primary Examiner—Larry Jones
Attorney, Agent, or Firm—Heslin, Watts & Rothenberg

[57] ABSTRACT

An improved heat exchanger mat and a method of dislodging and retrieving the mat from the bottom of a solar pond without disturbing an established thermal gradient. The mat is separated from the pond bottom by the injection of a dislodging medium between the mat and the bottom of the pond. When the pond contains a liner, the dislodging medium is injected between the mat and the pond liner. The mat (10) utilizes a dual conduit network of one integral conduit (12) for the flow of heat exchanger fluid and a second integral conduit (26) for the flow of dislodging medium. The dislodging medium enters the dislodging conduit via an inlet (28) and exits through a plurality of outlets (30) located on the underside of the mat. The medium, as it exits, forces the mat upward and frees it from the bottom of the pond. Once the dislodging medium has separated the mat from the pond bottom, attached retrieval cords (20) are used to remove the mat by drawing it up the side of the pond.

16 Claims, 4 Drawing Figures

HEAT EXCHANGER MAT

FIELD OF THE INVENTION

This invention relates to heat exchangers used in solar ponds.

BACKGROUND AND SUMMARY OF THE INVENTION

A solar pond works upon the principle that a shallow pond placed in the sun and having a salt density gradient increasing toward the bottom of the pond will produce a usable amount of heat energy in the lower layers. The heat from these lower layers is then drawn off and generally used for either space or water heating or in certain situations electricity generation. In order to prevent the seepage of salt water from the pond which could contaminate local ground water, a liner is generally placed in the pond.

With reports indicating that temperature above 200° F. have been obtained at the lower layers of some of the ponds presently in use, there is little doubt that the potential energy supply is significant if the heat can be suitably transferred out of the pond. Developing a workable and economically feasible apparatus for removing this heat has been difficult.

One early attempt to remove heat from these lower layers utilized ponds that were manufactured with inlet and outlet pipes opening into the most heated portion of the pond. By this method, the brine solution was drawn from the pond, circulated to a heat exchanger and returned to the pond. One difficulty with this system was that it was sometimes very time consuming and difficult to place the inlet and outlets in such a configuration that the movement of the brine would not disrupt the gradient within the pond. In addition, due to the fact that the brine is highly corrosive of metals, there was also an exceptional amount of wear on the piping used for the inlets and outlets and also on those portions of the heat exchanger which were in contact with the brine.

Another method of withdrawing heat from a solar pond involves the placement of a tubing on the bottom of the pond. As indicated above, where this tubing is made of metal or another corrosive material, the brine solution would cause a quick deterioration. While this method would allow for water to pass through the tubing avoiding contact with the brine solution, the positioning of the tubing was somewhat difficult. This is especially true in those situations wherein the tubing had to be removed to check for leaks or to in some way fix the passageway and the user was faced with a difficult task of trying to place the tubing back into the pond in an advantageous configuration.

In order to overcome some of the problems common to solar ponds and heat exchangers being used, the inventor began working on a new mat-type heat exchanger. One major advantage of utilizing a mat-type heat exchanger having conduits within the mat for circulation of heat exchanging liquid is the ability to provide a second layer of protection for the pond lining. By utilizing a redundant bottom lining, there is less likelihood of seepage which can contaminate ground waters. In addition, the mat can simply be placed on the surface of the pond where, due to the combined weight of the mat and heat exchange fluid, it will sink to the bottom of the pond with the predetermined conduit configurations intact as part of the mat. By manufacturing the mat out of a non-corrosive material, it is also possible to avoid the corroding effects of the brine solution.

While there are several advantages to the use of such a mat as a heat exchanger, one significant difficulty arose in that the mat and pond lining would form an adhesion which made removal of the mat difficult, especially without disrupting the salt gradient. The present invention overcomes this difficulty.

It is therefore an object of this invention to provide a heat exchanger which would aid in preventing seepage from the pond.

Another object of this invention is to provide a heat exchanger which can easily be separated and removed from the bottom of the pond.

Yet another object of this invention is to provide a heat exchanger which is easy to place in the pond with the heat exchanging conduits in the preferred and predetermined position.

Another object is to provide a heat exchanger which is not adversely affected by the brine solution in the pond.

Still another object of this invention is to provide a heat exchanger, the use of which does not disrupt the salt gradient within the pond.

Another object of this invention is to provide a heat exchanger which is economical to manufacture and operate.

Briefly described, the present invention comprises, in its preferred embodiment, an improved heat exchanger mat consisting of a flexible membrane having at least two conduits integrally associated therewith. The first conduit is utilized for heat exchange in that it is designed for the reception, circulation and discharge of a heat exchanging fluid. Heat from the solar pond is absorbed by the heat exchanging fluid as it circulates through the conduit. The first conduit generally has one inlet and one outlet so that the heated fluid can be recovered and transported to wherever it is to perform its thermal function. The second conduit has one inlet and a plurality of outlets located on one side of the membrane so that any medium, usually fluid, injected into the second conduit will exit through the openings thus forming a fluid layer beneath the mat that dislodges the mat from the bottom of the pond and from the solar pond liner and allows it to slide edgewise along the surface of the liner and out of the pond without disrupting the pond's thermal gradient.

Also briefly described, the present invention further consists of a method for removing a heat exchanger mat from the bottom of the solar pond without disturbing the thermal gradient. To accomplish this end, the heat exchanger mat is separated from the bottom of the pond by introducing a layer of separating medium between the mat and the pond bottom. The separating medium is introduced from the heat exchanger mat via a dislodging conduit having a plurality of outlets located on one side of the mat. If the solar pond contains a pond liner, the dislodging conduit may be located either in the heat exchanger mat or the liner. Retrieval cords, attached to the mat, are used to draw the mat sideways out of the pond.

The invention also encompasses a solar pond incorporating the above described features.

DETAILED DESCRIPTION OF THE DRAWINGS

Figure 1:
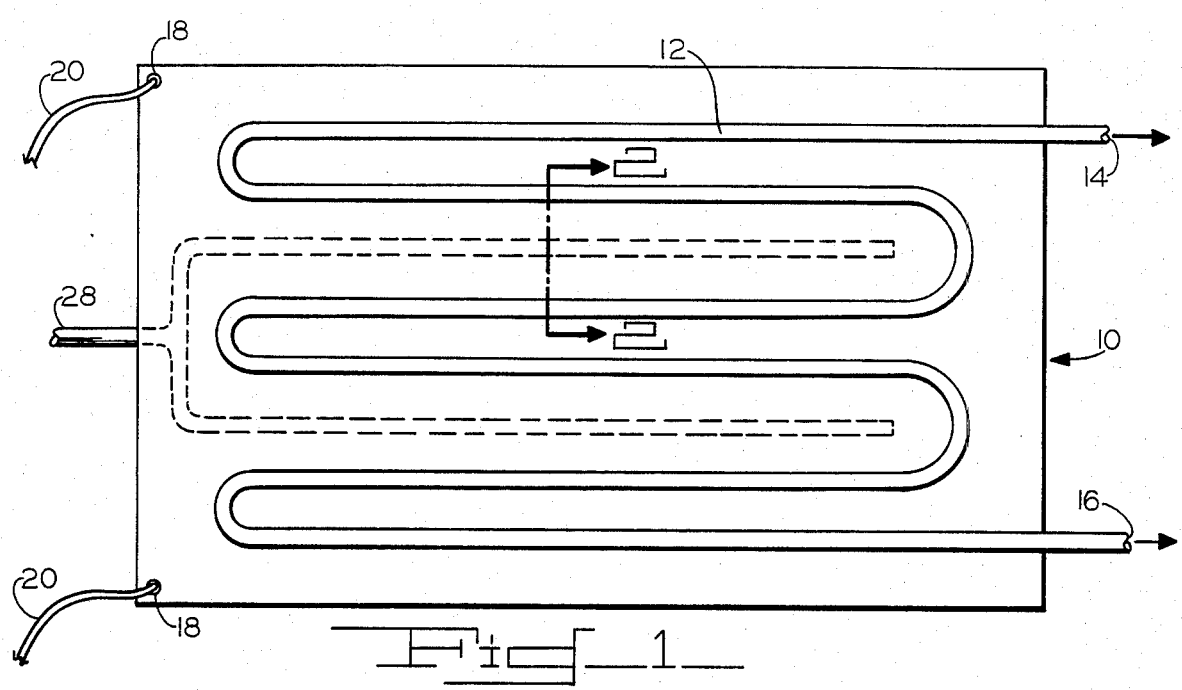
FIG. 1 is a top plan view of the invention showing the heat exchanger conduit.

The top view of heat exchanger mat 10 is illustrated in FIG. 1 showing heat exchanger conduit 12 represented in a preferred sinusoidal pattern. The particular configuration of exchanger conduit 12 is of little significance provided that the total length between exchanger inlet 14 and exchanger outlet 16 is sufficient to enable the maximum transfer of heat from the solar pond to the heat exchanger fluid. O-rings 18 are located at each of two corners of mat 10 and are shown having retrieval cords 20 attached. Mat 10 is shown having a rectangular shape, however, it will be understood by those skilled in the art that the geometric shape may vary and in some instances may correspond to that of the solar pond.

Figure 2:
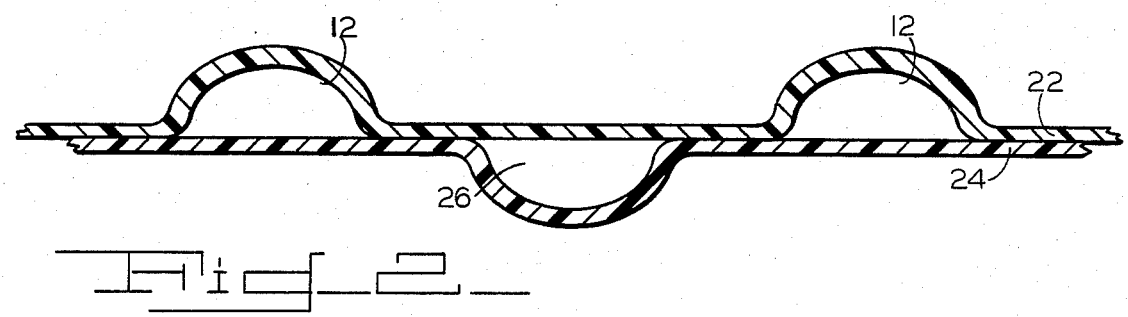
FIG. 2 is an enlarged cross-sectional view taken along lines 2—2 of FIG. 1 showing a double layer construction of the invention.

FIG. 2 shows the cross-sectional view of FIG. 1 taken along lines 2—2. One type of construction utilized for mat 10 is to seal two layers of flexible material together to form the desired network of conduits. As illustrated in FIG. 2, top layer 22 and bottom layer 24 are sealed to form exchanging conduit 12 and dislodging conduit 26. When this type of double layer construction is used to maintain the separation of the heat exchanging fluid and the dislodging medium, the two conduit pathways cannot be permitted to intersect. One alternate type of construction would be to use separate tubular conduits sealed to a single layer membrane, one on top to be used for exchanger conduit 12 and one on the bottom for the dislodging conduit 26. A second alternate construction would be to use a triple layer construction whereby the top and middle layers are sealed to form exchanger conduit 12 and the bottom and middle layers are sealed to form dislodging circuit 26. The materials used must be of sufficient density to permit mat 10, when filled with exchanging fluid, to sink to the bottom of the solar pond. If the thermal gradient in the pond is maintained using salt, then the density of the mat must be greater than that used for a fresh water pond. The material itself should be dense enough to automatically provide the correct negative buoyancy, if not, pockets of a more dense material, such as sand, can be formed into the finished product. It is also important that the materials used be flexible and, especially when the mats are being placed into concentrated saline, non-corrosive. Polymeric or elastomeric materials are suitable for this purpose.

Figure 3:
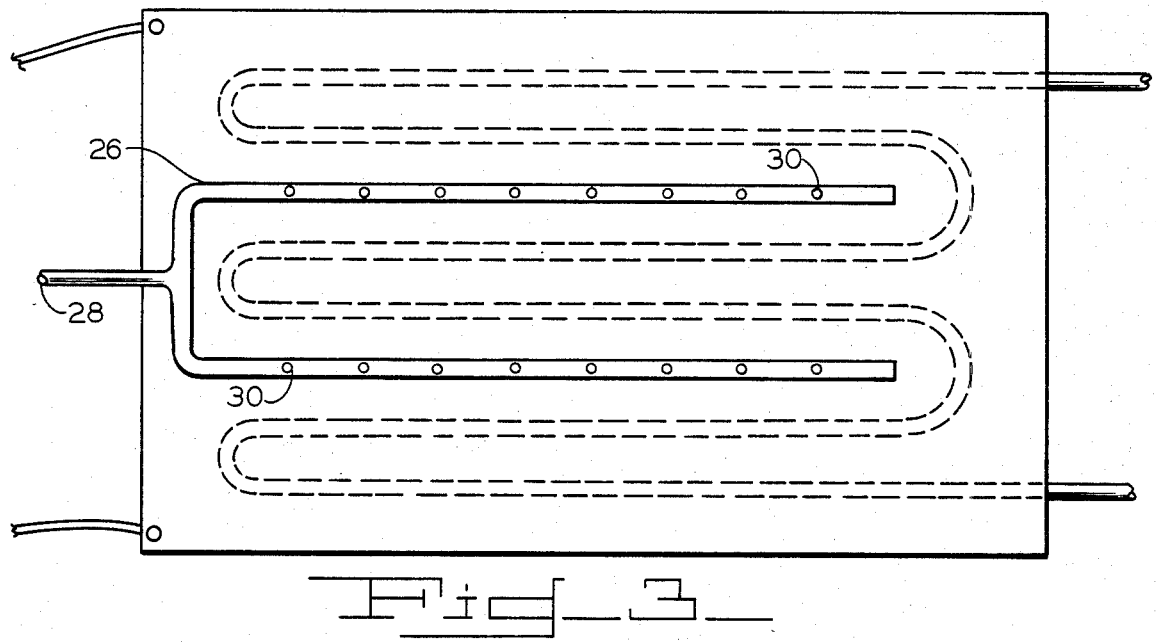
FIG. 3 is a bottom view of the invention showing the dislodging conduit.

The bottom view of the invention as shown in FIG. 3, more clearly illustrates dislodging conduit 26. The U-shaped configuration is a convenient representation of dislodging conduit 26 and is not intended to be limiting. Medium, generally fluid, is injected into dislodging conduit 26 via dislodging inlet 28 which then exits through dislodging outlets 30. The force of the fluid as it exits through outlets 30 raises mat 10 above the pond bottom, thus permitting its removal without disturbing the thermal gradient by drawing the mat up the side of the pond using retrieval cords 20.

In actual operation, heat exchanger mat 10 is floated onto the surface of the solar pond. The solar pond is generally made by digging a shallow depression in the ground and lining it with a suitable flexible liner. The liner is required to prevent loss of salt water into the ground and possible contamination of the local ground water. Heat exchanger conduit 12 is filled with fluid, usually fresh water, and the combined weight of the water and the density of mat 10 will cause the unit to sink to the bottom of the pond. Circulation of the fluid through exchanger conduit 12 is maintained by an externally located pump (not shown). While mat 10 is functioning in its heat exchanging capacity, dislodging conduit 26 remains empty and inoperative. When it becomes necessary to retrieve mat 10, a dislodging fluid is introduced into dislodging conduit 26 via dislodging inlet 28, the appropriate connective tubing for this purpose having been attached prior to the sinking of mat 10. If the solar pond is one having a salt gradient, the dislodging fluid should also be a salt solution having a concentration close to that maintained on the bottom of the pond in order to avoid disturbing the established salt gradient. The fluid flows into dislodging conduit 26 and exits through the plurality of dislodging outlets 30. Outlets 30 are usually located on the underside of mat 10 so that the fluid is directed downward toward the bottom of the pond and against the pond liner. The amount of dislodging fluid and the required force of injection depend on the magnitude of the friction and adhesive forces existing between mat 10 and the pond liner. Generally, the longer mat 10 has been in its operative position, the greater these forces will be. Once a sufficient amount of fluid has been forced to exit through outlets 30, mat 10 will separate from the pond liner and "float" above the bottom of the pond. Retrieval cords 20 then allow mat 10 to be drawn out of the pond easily, along the surface of the liner, without disruption of the thermal gradient.

Figure 4:
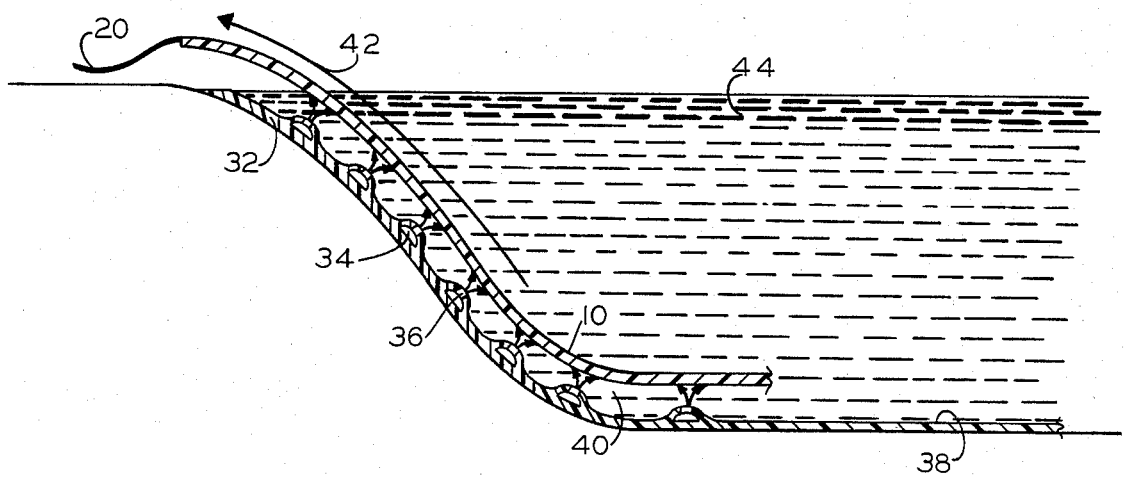
FIG. 4 is a side view of a part of a solar pond incorporating an alternate embodiment of the invention.

Alternatively, as illustrated in FIG. 4, the separation of the heat exchanger mat 10 and the pond liner 32 could be accomplished by locating the disloding conduit 34 in the pond liner. The dislodging outlets 36 would then be placed in the top surface 38 of the liner so that the dislodging medium 40 would be forced upward towards the mat in order to separate the mat from the liner. The mat, thus freed from and elevated slightly above surface 38 of the liner, can be drawn along the surface of the liner, in the direction generally shown by arrow 42, and out of the solar pond 44, without disrupting the pond's thermal gradient.

Thus, it can be seen that this invention accomplishes at least all of its stated objectives. While the above description has been directed towards the extraction and transfer of heat from a solar pond, the invention can be used with equal facility for the reverse transfer of heat to a large body of water. It is to be understood that various changes and modifications may be made therein without departing from the spirit of the invention and the spirit and scope of the appended claims.

I claim:

1. An improved heat exchanger mat for placement upon the bottom surface of a solar pond comprising:
   a flexible membrane having
   a first conduit for the reception, circulation and discharge of a heat exchanging fluid,
   a second conduit for the reception and discharge of a dislodging medium, said conduit having a plurality of outlets opening on one side of the membrane; and means for withdrawing the mat from the solar pond without disturbing the thermal gradient within the pond.

2. The invention of claim 1 wherein the flexible membrane comprises a top and bottom layer sealed to form the first and second conduit.

3. The invention of claim 1 wherein the flexible membrane is made of a non-corrosive material.

4. The invention of claim 3 wherein the non-corrosive material is polymeric.

5. The invention of claim 3 wherein the non-corrosive material is elastomeric.

6. The invention of claim 1 wherein the means for withdrawing the mat comprises means for drawing the mat edgewise along the bottom surface of the pond and out of the solar pond.

7. The invention of claim 1 further comprising a dislodging medium comprising brine.

8. The invention of claim 7 wherein the brine has substantially the same salt concentration as liquid near the bottom surface of the solar pond.

9. A method for removing a heat exchanger mat from its operative position on the bottom surface of a solar pond without disturbing the thermal gradient within the pond comprising the steps of:
separating the mat from the bottom surface of the pond by introducing medium under the mat; and
drawing the mat along said bottom surface and out of the pond.

10. The method of claim 9 wherein the step of separating further comprises:
providing the mat with a conduit having an inlet and a plurality of outlets;
introducing medium through the inlet; and
forcing the mat upward to an adjacent, nonabutting position with respect to the bottom surface, by discharging the medium through the outlets downward towards the bottom surface of the pond.

11. Solar pond apparatus comprising:
a repository for fluid;
a liner located along the bottom of the repository, the liner having a first surface exposed to said fluid;
fluid in the repository, said fluid exhibiting a thermal gradient when exposed to solar energy;
heat exchanger means located within the fluid repository adjacent the first surface of the liner; and
means for extracting the heat exchanger means from the repository without disturbing the thermal gradient in the fluid.

12. The apparatus of claim 11 wherein the extracting means comprises:
first means for separating the heat exchanger means from the first surface of the liner; and
second means for displacing the heat exchanger means along said first surface and out of the repository.

13. The apparatus of claim 12 wherein the heat exchanger means comprises a mat including a flexible membrane having a conduit for the reception, circulation and discharge of a heat exchanging fluid; and
wherein said first means comprises means for introducing medium between the first surface of the liner and the mat for separating them from one another.

14. The apparatus of claim 13 wherein the fluid in the repository comprises a salt solution, the concentration of salt in said solution varying with depth; and
wherein said medium comprises a salt solution having a concentration of salt substantially the same as the fluid near the bottom of the repository.

15. The invention of claim 13 wherein the means for introducing medium comprises the membrane having a second conduit for the reception and discharge of a dislodging medium, said conduit having a plurality of outlets opening on one side of the membrane.

16. The invention of claim 13 wherein the means for introducing medium comprises the liner having a conduit for reception and discharge of a dislodging medium, said conduit having a plurality of perforations located on said first surface of the liner.

* * * * *